United States Patent [19]

Lohaus et al.

[11] Patent Number: 4,797,409
[45] Date of Patent: Jan. 10, 1989

[54] 1-HYDROXY-2-PYRIDONES, A PROCESS FOR THEIR PREPARATION, AND MEDICAMENTS WHICH CONTAIN THEM, AND INTERMEDIATES FORMED IN THE PREPARATION OF THE 1-HYDROXY-2-PYRIDONES

[75] Inventors: Gerhard Lohaus, Kelkheim; Walter Dittmar, Hofheim am Taunus; Heinz Hänel, Bad Homburg; Wolfgang Raether, Dreieich; Dieter Reuschling, Butzbach; Bengt-Thomas Gröbel, Bad Soden am Taunus, all of Fed. Rep. of Germany

[73] Assignee: Hoechst Aktiengesellschaft, Fed. Rep. of Germany

[21] Appl. No.: 38,903

[22] Filed: Apr. 16, 1987

[30] Foreign Application Priority Data

Apr. 18, 1986 [DE] Fed. Rep. of Germany ....... 3613061
Aug. 2, 1986 [DE] Fed. Rep. of Germany ....... 3626211

[51] Int. Cl.$^4$ .............................................. A61K 31/44
[52] U.S. Cl. .................................... 514/345; 546/301; 546/302
[58] Field of Search ................. 546/301, 302; 514/345

[56] References Cited

U.S. PATENT DOCUMENTS

| | | | |
|---|---|---|---|
| 2,540,218 | 2/1951 | Shaw | 546/290 |
| 3,269,904 | 8/1966 | Bernstein | 546/290 |
| 3,883,545 | 5/1975 | Lohaus et al. | 546/283 |
| 3,968,118 | 7/1976 | Lohaus et al. | 546/283 |
| 3,972,888 | 8/1976 | Lohaus et al. | 546/283 |
| 4,185,106 | 1/1980 | Dittmar et al. | 546/301 |

FOREIGN PATENT DOCUMENTS

2234009  3/1974  Fed. Rep. of Germany ...... 546/301

OTHER PUBLICATIONS

Lohaus et al., Arz. Forsch/Drug Res., vol. 31 (II), No. 8a (1981), "Zur Chemie Von Antimikrobiell Wirksamen 1-Hydroxy-2-Pyridonen".
Chemical Abstracts, vol. 79, No. 25, Abstract: 146419w, p. 316, Dec. 24, 1973.
Chemische Berichte, 100, pp. 658–677 (1967).

*Primary Examiner*—Mary C. Lee
*Assistant Examiner*—Zinna Northington
*Attorney, Agent, or Firm*—Finnegan, Henderson, Farabow, Garrett & Dunner

[57] ABSTRACT

New 1-hydroxy-2-pyridones of the general formula I

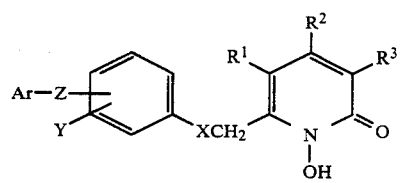

in which
$R^1$, $R^2$ and $R^3$, which are identical or different, denote hydrogen or lower alkyl having 1–4 carbon atoms, $R^1$ and $R^3$ preferably being hydrogen, and $R^2$ preferably being methyl,
X denotes S or, preferably, O,
Y denotes hydrogen or up to 2 halogen atoms, namely chlorine and/or bromine,
Z denotes a single bond or the bivalent radicals O, S, —CR$_2$— (R=H or C$_1$–C$_4$-alkyl) or other 2-valent radicals with 2–10 carbon and, optionally, oxygen and/or sulfur atoms linked to form a chain, it being obligatory when the radicals contain 2 or more oxygen and/or sulfur atoms for the latter to be separated by at least 2 carbon atoms, and it being possible for 2 adjacent carbon atoms also to be linked together by a double bond, and the free valencies of the carbon atoms being saturated by H and/or C$_1$–C$_4$-alkyl groups,
Ar denotes an aromatic ring system which has up to two rings and can be substituted by up to three radicals from the group comprising fluorine, chlorine, bromine, methoxy, C$_1$–C$_4$-alkyl, trifluoromethyl and trifluoromethoxy, are prepared by a variety of process variants. The compounds and their physiologically tolerated salts with inorganic or organic bases mainly have antimycotic, anti-bacterial and antiviral activity. The compounds of the formula V

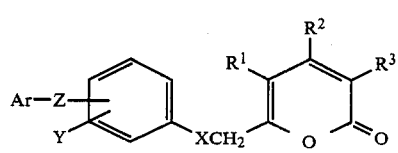

in which $R^1$, $R^2$, $R^3$, X, Y, Z and Ar have the same meaning as in formula I, which occur in the preparation of the compounds of the formula I, are also new.

15 Claims, No Drawings

1-HYDROXY-2-PYRIDONES, A PROCESS FOR THEIR PREPARATION, AND MEDICAMENTS WHICH CONTAIN THEM, AND INTERMEDIATES FORMED IN THE PREPARATION OF THE 1-HYDROXY-2-PYRIDONES

The invention relates to new 1-hydroxy-2-pyridones of the general formula I (see patent claim 1), to their use for controlling, in the main, infections by fungi and yeasts, and to medicaments which contain these compounds; the invention also relates to specific intermediates formed in the preparation of the new 1-hydroxy-2-pyridones.

German Pat. No. 2,234,009 discloses compounds of the formula II

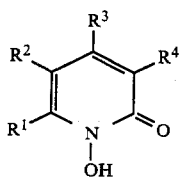

in which $R^1$ denotes, inter alia, aryloxyalkyl or arylmercaptoalkyl with alkyl of 1-4 carbon atoms. The only specific illustrations of these radicals are phenyloxymethyl or phenylmercaptomethyl. According to German Pat. No. 2,234,009, apart from aryloxyalkyl or arylmercaptoalkyl, $R^1$ can also represent various other radicals such as aryl, aralkyl with alkyl of 1-4 carbon atoms, arylalkenyl with alkenyl of 2-4 carbon atoms, benzhydryl and phenylsulfonylalkyl with alkyl of 1-4 carbon atoms. Where specifications are stated in the said patent for these radicals, they are always—with the exception of the aryl radical itself, which is also stated as naphthyl—only phenyl radicals which are optionally substituted by alkyl groups having 1-4 carbon atoms, alkoxy groups having 1-4 carbon atoms, nitro groups, cyano groups or halogen.

In contrast to this, the invention relates to those 1-hydroxy-2-pyridone derivatives in which the substituent in the 6-position ($R^1$ in formula II) contains an aromatic system which contains at least 2 isolated, optionally substituted aromatic rings and is bonded via an oxymethyl group or a thiomethyl group to the pyridone residue, and which derivatives are described by the general formula I.

Thus the invention relates to 1-hydroxy-2-pyridones of the general formula I (see patent claim 1) in which
$R^1$, $R^2$ and $R^3$, which are identical or different, denote hydrogen or lower alkyl having 1-4 carbon atoms, $R^1$ and $R^3$ preferably being hydrogen, and $R^2$ preferably being methyl,
X denotes S or, preferably, O,
Y denotes hydrogen or up to 2 halogen atoms, namely chlorine and/or bromine,
Z denotes a single bond or the bivalent radicals O, S, —CR$_2$— (R=H or C$_1$–C$_4$-alkyl) or other 2-valent radicals with 2-10 carbon and, optionally, oxygen and/or sulfur atoms linked to form a chain, it being obligatory when the radicals contain 2 or more oxygen and/or sulfur atoms for the latter to be separated by at least 2 carbon atoms, and it being possible for 2 adjacent carbon atoms also to be linked together by a double bond, and the free valencies of the carbon atoms being saturated by H and/or C$_1$–C$_4$-alkyl groups,
Ar denotes an aromatic ring system which has up to two rings and can be substituted by up to three identical or different radicals from the group comprising fluorine, chlorine, bromine, methoxy, C$_1$–C$_4$-alkyl, trifluoromethyl and trifluoromethoxy.

The C chain members in the radicals Z are preferably CH$_2$ groups. When the CH$_2$ groups are substituted by C$_1$–C$_4$-alkyl groups, the preferred substituent are CH$_3$ and C$_2$H$_5$. Examples of radicals Z are: —O—, —S—, —CH$_2$—, —(CH$_2$)$_m$— (m=2-10), —C(CH$_3$)$_2$—, —CH$_2$O—, OCH$_2$—, —CH$_2$S—, —SCH$_2$—, —SCH(C$_2$H$_5$)—, —CH=CH—CH$_2$O—, —O—CH$_2$—CH=CH—CH$_2$O—, —OCH$_2$CH$_2$O—, —OCH$_2$CH$_2$CH$_2$O—, —SCH$_2$CH$_2$CH$_2$S—, —SCH$_2$CH$_2$CH$_2$CH$_2$O—, —SCH$_2$CH$_2$OCH$_2$CH$_2$O—, —SCH$_2$CH$_2$OCH$_2$CH$_2$O—CH$_2$CH$_2$S—, —S—CH$_2$—C(CH$_3$)$_2$—CH$_2$—S—, etc.

The term aromatic ring system embraces phenyl and fused systems such as naphthyl, tetrahydronaphthyl and indenyl, as well as isolated systems such as those derived from biphenyl, diphenylalkanes, diphenyl ethers and diphenyl thioethers.

Examples of important representatives of the class of compounds defined by the formula I are 6-[4-(4-chlorophenoxy)phenoxymethyl]-1-hydroxy-4-methyl-2-pyridone, melting point 167° C. (1), 6-[4-(2,4-dichlorophenoxy)phenoxymethyl]-1-hydroxy-4-methyl-2-pyridone, melting point 162° C. (2), 6-(biphenylyl-4-oxymethyl)-1-hydroxy-4-methyl-2-pyridone, melting point 184° C. (3), 6-(4-benzylphenoxymethyl)-1-hydroxy-4-methyl-2-pyridone, melting point 149° C. (4), 6-[4-(2,4-dichlorobenzyloxy)phenoxymethyl]-1-hydroxy-4-methyl-2-pyridone, melting point 172° C. (5), 6-[4-(4-chlorophenoxy)phenoxymethyl]-1-hydroxy-3,4-dimethyl-2-pyridone, melting point 155° C. (6), 6-[4-(2,4-dichlorobenzyl)phenoxymethyl]-1-hydroxy-3,4-dimethyl-2-pyridone, melting point 169° C. (7), 6-[4-(cinnamyloxy)phenoxymethyl]-1-hydroxy-4-methyl-2pyridone, melting point 179° C. (8), 1-hydroxy-4-methyl-6-[4-(4-trifluoromethylphenoxy)phenoxymethyl]-2-pyridone, melting point 149° C. (9), 1-hydroxy-4-methyl-6-[4-(1-naphthylmethoxy)phenoxymethyl]-2-pyridone, melting point 179° C. (10), 6-[4-(4-chlorophenoxy)phenoxymethyl]-1-hydroxy-4,5-dimethyl-2-pyridone (11), 6-[4-(4-(4-chlorophenoxy)phenoxymethyl)phenoxymethyl]-1-hydroxy-4-methyl-2-pyridone, melting point 158° C. (12), 6-[2,6-dichloro-4-(2-naphthylthiomethyl)phenoxymethyl]-1-hydroxy-4-methyl-2-pyridone, melting point 138° C. (13), 6-[2,6-dichloro-4-(4-phenylphenoxymethyl)phenoxymethyl]-1-hydroxy- 4-methyl-2-pyridone, melting point 190° C. (14), 6-[4-(4-chlorobenzyloxy)phenoxymethyl]-1-hydroxy-4-methyl-2-pyridone, melting point 173° C. (15), 1-hydroxy-4-methyl-6-[4-(4-trifluoromethoxybenzyloxy)phenoxymethyl]-2-pyridone, melting point 143° C. (16), 6-[4-(4-tert.-butylbenzyloxy)phenoxymethyl]-1-hydroxy-4-methyl-2-pyridone, melting point 181° C. (17), 6-[2-(4-chlorobenzyloxy)phenoxymethyl]-1-hydroxy-4-methyl-2-pyridone, melting point 161° C. (18), 1-hydroxy-4-methyl-6-[2-(naphth-1-ylmethoxy)phenoxymethyl]-2-pyridone, melting point 150° C. (19), 1-hydroxy-4-methyl-6-[3-(1-naphthylmethoxy)phenoxymethyl]-2-pyridone, melting point 155° C. (20), 6-[3-(4-chlorobenzyloxy)phenoxymethyl]-1-hydroxy-4-methyl-2-pyridone, melting point 149° C. (21), 6-[4-(4-chlorophenoxy)phenoxymethyl]-1-hydroxy-2-pyridone, melting point 180° C. (22), 6-[2,6-dichloro-4-(4-chlorophenoxy)-phenoxymethyl]-1-hydroxy-4-methyl-2-pyridone, melting point 150° C. (23), 6-(4-benzyloxy-2,6-dichlorophenoxymethyl)-1-hydroxy-4-methyl-2-pyridone, melting point 161° C. (24), 6-(2,6-dichloro-4-phenylphenoxymethyl)-1-hydroxy-4-methyl-2-pyridone, melting point 195° C. (25), 6-[4-(4-bromo-2-chlorophenoxy)-phenoxymethyl]-1-hydroxy-4-methyl-2-pyridone, melting point 174° C. (26), 1-hydroxy-4-methyl-6-[4-(3,4,5-trimethoxybenzyloxy)phenoxymethyl]-2-pyridone, melting point 154° C. (27), 6-[4-(2,4-dichlorobenzyl)-phenoxymethyl]-1-hydroxy-4-methyl-2-pyridone, melting point 173° C. (28), 6-[2,6-dibromo-4-(4-chlorophenoxy)phenoxymethyl]-1-hydroxy-4-methyl-2-pyridone (29), 6-(2,6-dibromo-4-phenylphenoxymethyl)-1-hydroxy-4-methyl-2-pyridone (30), 6-(2-bromo-4-phenylphenoxymethyl)-1-hydroxy-4-methyl-2-pyridone, melting point 245° C. (31), 6-(2-bromo-6-chloro-4-phenylphenoxymethyl)-1-hydroxy-4-methyl-2-pyridone (32), 6-[4-(4-fluorophenoxy)phenoxymethyl]-1-hydroxy-4-methyl-2-pyridone, melting point 151° C. (33), 6-[3-(4-chlorophenylthio)phenoxymethyl]-1-hydroxy-4-methyl-2-pyridone (34), 1-hydroxy-4-methyl-6-[3-(1-naphthylmethylthio)phenoxymethyl]-2-pyridone, melting point 144° C. (35), 1-hydroxy-4-methyl-6-[3-(1-naphthylmethoxy)phenylthiomethyl]-2-pyridone, melting point 163° C. (36), 1-hydroxy-4-methyl-6-(2-phenylphenoxymethyl)-2-pyridone, melting point 179° C. (37), 6-(2-benzylphenoxymethyl)-1-hydroxy-4-methyl-2-pyridone, melting point 155° C. (38), 1-hydroxy-3,4-dimethyl-6-[3-(1-naphthylmethylthio)phenoxymethyl]-2-pyridone, melting point 143° C. (39), 6-(2,4-dibromo-6-phenylphenoxymethyl)-1-hydroxy-4-methyl-2-pyridone, melting point 130° C. (40), 6-[4-(4-(4-chlorophenoxy)phenoxy)phenoxymethyl]-1-hydroxy-4-methyl-2-pyridone, melting point 100° C. (41), 6-[3-(4chlorobenzyloxy)phenylthiomethyl]-1-hydroxy-4-methyl-2pyridone, melting point 94° C. (42), 6-[4-(4-chlorophenylthio)phenoxymethyl]-1-hydroxy-4-methyl-2-pyridone, melting point 158° C. (43), 1-hydroxy-6-[4-(4-methoxyphenylthio)phenoxymethyl]-4-methyl-2-pyridone, melting point 162° C. (44), 1-hydroxy-4-methyl-6-[3-(2-phenoxyethoxy)phenoxymethyl]-2-pyridone, melting point 148° C. (45), 6-[4-(4-chlorophenoxypropoxy)phenoxymethyl]-1-hydroxy-4-methyl-2-pyridone, melting point 162° C. (46), 6-[3-(4-chlorophenylthiopropylthio)phenoxymethyl]-1-hydroxy-4-methyl-2-pyridone, melting point 102° C. (47), 6-[3-(4-chlorophenylthiobutoxy)phenoxymethyl]-1-hydroxy-4-methyl-2-pyridone, melting point 104° C. (48), 6-[3-(4-chlorophenylthioethoxyethoxy)phenoxymethyl]-1-hydroxy-4-methyl-2-pyridone, melting point 98° C. (49), 6-[4-(α,α-dimethyl-4-methoxybenzyl)phenoxymethyl]-1-hydroxy-4-methyl-2-pyridone, melting point 156° C. (50), 6-<3-[1-(4-chlorophenylthio)-2,2-dimethylprop-3-ylthio]phenoxymethyl>-1-hydroxy-4-methyl-2-pyridone, melting point 134° C. (51), 6-<4-[1-(4-chlorophenyl)but-2-en-4-yloxy]phenoxymethyl>-1-hydroxy-4-methyl-2-pyridone, melting point 167° C. (52), 6-[3-(4-chlorophenylthioethoxyethoxyethylthio)-phenoxymethyl]-1-hydroxy-4-methyl-2-pyridone, melting point 95° C. (53), 6-<4-[1-(4-chlorophenyl)-5-pentyl]phenoxy-methyl>-1-hydroxy-4-methyl-2-pyridone, melting point 159° C. (54).

The compounds according to the invention can be prepared by various ways known per se, for example by reaction of 6-halogenomethyl-2-pyrones of the formula III (see patent claim 9) with phenols or thiophenols of the formula IV (see patent claim 9), which are optionally suitably substituted, and conversion of the aryloxymethylpyrones or arylthiomethylpyrones of the formula V (see patent claim 9) which are formed into the hydroxypyridones by the action of hydroxylamine. The alkylations are expediently carried out in protic or aprotic solvents such as methanol, ethanol, isopropanol, acetone, acetonitrile, ethylene glycol dimethyl ether, diethylene glycol dimethyl ether, dimethylformamide or dimethyl sulfoxide, preference being given to the aprotic solvents. To bind the hydrogen halide which is being liberated, inorganic or organic bases such as sodium or potassium hydroxide, sodium, potassium or calcium carbonate, triethylamine, tributylamine, pyridine, 4-dimethylaminopyridine, diazabicyclononane, N-methylpiperidine, inter alia, are used in at least equivalent amounts. The reaction temperatures are, in general, between room temperature and about 80° C.; however, in special cases, distinctly higher or lower temperatures may be advantageous, such as 110° C. or 0° C. To convert the 2-pyrones into the 1-hydroxy-2-pyridones, the hydroxylamine is generally reacted in the form of its salts with inorganic or organic acids, preferably with hydrochloric sulfuric or acetic acid, in the presence of at least about one equivalent of a base relative to the hydroxylammonium salt. The amount of the hydroxylamine salt is at least about 1 mole relative to the pyrone used; however, it is favorable, to increase the reaction rate and the yield, to use an excess, say between 2 and 10 moles relative to one mole, and, moreover, to add this amount in several portions during the reaction time. Suitable bases for this reaction are both organic and inorganic bases. Preferred organic bases are aminopyridine (derivatives) and imidazole (derivatives) such as 2-aminopyridine, 2-aminopicoline, 2-methylaminopyridine, imidazole and 2-methylimidazole; preferred inorganic bases are the carbonates and/or bicarbonates of the alkali metals ($Li_2CO_3$, $Na_2CO_3$, $K_2CO_3$, $NaHCO_3$, $KHCO_3$, $Rb_2CO_3$, $CsHCO_3$ etc.). Of the inorganic bases mentioned, the carbonates and bicarbonates of sodium and potassium, especially $Na_2CO_3$, are especially suitable.

The organic bases are generally used in amounts between about 1 and 20 moles, preferably between about 3 and 10 moles, per mole of the pyrone used, and can simultaneously act as solvents; this normally also fulfils the condition that at least about 1 equivalent of base is present with reference to the hydroxylammonium salt used.

Of course, it is also possible to use mixtures of these bases, for example to reduce the melting range of the system if the process is to be carried out at low temperatures. In general, the reaction temperatures for this are between about 20° C. and 150° C., preferably between about 50° C. and 100° C.

In the case where the inorganic bases are used, it is expedient, as with the organic bases, to add an amount which is at least approximately equivalent to the amount of hydroxylammonium salt used. For example, at least ½ mole of $Na_2CO_3$ or 1 mole of $NaHCO_3$ should be used per mole of hydroxylammonium chloride. It is also possible for the inorganic bases to be used both singly and in any desired mixture.

To carry out the variant with the inorganic bases, it is advantageous to mix the 2-pyrone with the hydroxylammonium salt, in this case preferably with the hydroxylammonium sulfate, and with the alkali metal carbonate and/or bicarbonate and to heat the resulting mass of crystals until the pyrone has been converted as far as possible; after removal of the inorganic salts, the resulting 2-pyridone can be isolated directly or, better, as the salt of an organic base, for example as the ethanolamine salt.

The temperature at which this variant is carried out should on no account exceed about 120° C. It is expediently above about 50° C. and preferably between about 60° and 105° C.

It is also possible, both in the variant with organic bases and that with inorganic bases, to add inert solvents or diluents. Although this is not generally necessary, it can have advantages in the individual case. If solvents or diluents are added, this generally takes place only in small amounts, usually up to about 50% by weight of the total reaction mixture. The preferred amount is about 3 to 15% by weight.

The solvents or diluents can be polar or non-polar and miscible or immiscible with water. Examples of substances which can be used are the following: water, low molecular-weight alcohols such as methanol, ethanol, isopropanol, ethylene glycol, ethylene glycol monomethyl ether and propylene glycol, amides such as dimethylformamide and diethylformamide, ethers such as diisopropyl ether, chlorinated hydrocarbons such as chlorobenzene, nitriles such as acetonitrile, or hydrocarbons which are aliphatic, cycloaliphatic or aromatic in nature.

The 6-halogenomethyl-2-pyrones, especially the chlorine compounds, can be prepared, for example, in the manner described in Chemische Berichte 100 (1967), page 658.

Another possibility for synthesizing the hydroxypyridones comprises side-chain halogenation of 2-halogeno-6-picolines to give 2-halogeno-6-halogenomethylpyridines of the formula VI (see patent claim 9), reaction of the halogenomethyl group with phenols which are optionally suitably substituted, oxidation to give the N-oxide and hydrolysis of the halogen on the nucleus by direct or indirect means. The reaction of the halogenomethyl group with the phenols is preferably carried out under conditions such as described above for the reaction of the halogenomethylpyrones with phenols. The oxidizing agents used for the conversion of the pyridines into their N-oxides are inorganic or organic, such as hydrogen peroxide, performic acid, peracetic acid, perbenzoic acid, 3-chloroperbenzoic acid and tert.-butyl hydroperoxide, and the conversion is carried out, where appropriate, with catalysis by a strong acid such as sulfuric acid, perchloric acid, toluenesulfonic acid, trifluoroacetic acid and trifluoromethanesulfonic acid, preferably between room temperature and about 100° C. The hydrolysis of the halogen on the nucleus can be carried out directly, for example by reaction with bases such as sodium hydroxide, potassium hydroxide or barium hydroxide, or indirectly via etherification with an alcohol which can in turn be easily eliminated again, such as tert.-butanol or 2-methoxyethanol.

Typical procedures for the preparation of the compounds of the general formula I, according to the invention, are illustrated by the examples which follow.

Where one of the abovementioned processes results in intermediates which still contain reactive substituents in Ar or the pyrone ring, it is possible via these substituents to introduce further groups where they correspond to the definitions $R^1$ to $R^3$ and the substituents indicated for Ar. For example, it is possible subsequently to etherify a free hydroxyl or mercapto group, or it is possible to convert a hydroxymethyl group, for example formed by reduction of an aldehyde group, into a halogenomethyl group, and then to exchange the halogen again nucleophilically with a phenol or thiophenol. It is also possible analogously to convert pyridine derivatives resulting from reaction of the dihalogenopicolines V with the phenols, or the N-oxides obtained therefrom by oxidation, which still contain reactive substituents, into substitution products of other types.

The invention also relates to the compounds of the formula V which are suitable as intermediates.

The compounds of the formula I, according to the invention, have excellent topical antimycotic properties with a broad spectrum of actions against pathogenic fungi such as dermatophytes (filamentous fungi) and those fungi which affect both the skin and the mucous membrane, such as yeasts (for example Candida spp.), as well as molds (for example *Aspergillus niger*). Hence they can be used for controlling infections caused by these pathogens in human and veterinary medicine, for example in domestic livestock such as dogs, cats and birds, and commercial livestock such as ruminants, horses and hogs. The hydroxypyridones can be used in the free form or as their physiologically tolerated salts with inorganic or organic bases (for example with NaOH, KOH, $Ca(OH)_2$, $NH_3$, $H_2NCH_2CH_2OH$ etc.) in the presentations customary for controlling fungi, such as solutions, suspensions, creams, ointments, powders or suppositories (vaginal tablets). The new products are distinguished, in particular, by their high fungicidal activity and a long retention time at the site of infection and, in this respect, are superior to standard commercial products, as will be shown in the comparison tests de-

EXAMPLES

1:
6-[4-(2,4-Dichlorobenzyl)phenoxymethyl]-1-hydroxy-3,4-dimethyl-2-pyridone (compound 7)

19.85 g of 6-chloromethyl-3,4-dimethyl-2-pyrone (compound A) and 25.3 g of 4-(2,4-dichlorobenzyl)phenol were dissolved in 70 ml of dimethylformamide, 20 g of finely ground potassium carbonate were added, and the mixture was stirred at room temperature for 48 hours. Then 200 ml of methylene chloride and 500 ml of water were added, the layers were separated, and the organic phase was washed twice with 100 ml of water each time, dried and evaporated under waterpump vacuum. The residue of 42.7 g was almost pure by thin-layer chromatography and was heated with 200 g of 2-aminopyridine at 75° C. for 56 hours and, during the first 41 hours, a total of 41.7 g of hydroxylamine hydrochloride was added in 5 portions. Then 250 ml of methylene chloride were added, and the organic phase was washed once with dilute hydrochloric acid and twice with water, and the solvent was removed by distillation under reduced pressure. The residue of 39.7 g was recrystallized from ethylene glycol monomethyl ether, and 32.5 g of pure hydroxypyridone of melting point 169° C. were obtained.

2 to 19

In the same manner as in Example 1, the compound 6 was obtained starting from 4-(4-chlorophenoxy)phenol and A, the compound 39 was obtained from 3-(1-naphthylmethylthio)phenol and A, the compound 1 was obtained from 4-(4-chlorophenoxy)phenol and 6-chloromethyl-4-methyl-2-pyrone (compound B), the compound 2 was obtained from 4-(2,4-dichlorophenoxy)phenol and B, the compound 9 was obtained from 4-(4-trifluoromethylphenoxy)phenol and B, the compound 23 was obtained from 2,6-dichloro-4-(4-chlorophenoxy)phenol and B, the compound 25 was obtained from 2,6-dichloro-4-phenylphenol and B, the compound 33 was obtained from 4-(4-fluorophenoxy)phenol and B, the compound 34 was obtained from 3-(4-chlorophenylthio)phenol and B, the compound 35 was obtained from 3-(1-naphthylmethylthio)phenol and B, the compound 40 was obtained from 2,4-dibromo-6-phenylphenol and B, the compound 41 was obtained from 4-[4-(4-chlorophenoxy)phenoxy]phenol and B, the compound 43 was obtained from 4-(4-chlorophenylthio)phenol and B, the compound 4 was obtained from 4-benzylphenol and B, the compound 38 was obtained from 2-benzylphenol and B, the compound 3 was obtained from 4-phenylphenol and B, the compound 26 was obtained from 4-(4-bromo-2-chlorophenoxy)phenol and B, and the compound 54 was obtained from 4-[1-(4-chlorophenyl)-5-pentyl]phenol and B.

20:
1-Hydroxy-4-methyl-6-[4-(1-naphthylmethoxy)phenoxymethyl]-2-pyridone (compound 10)

A mixture of 100 g of 6-chloromethyl-4-methyl-2-pyrone, 210 g of hydroquinone, 132 g of potassium carbonate and 400 ml of dimethylformamide was stirred at room temperature for 72 hours, water was added, the mixture was neutralized with hydrochloric acid, and the precipitate was filtered off with suction, washed with water and dried. By treatment with methylene chloride followed by recrystallization from acetonitrile, 68 g of virtually pure 6-(4-hydroxyphenoxymethyl)-4-methyl-2-pyrone of melting point 179° C. were obtained. 4.8 g of this compound were stirred with 4 g of 1-chloromethylnaphthalene, 20 ml of dimethylformamide and 8 g of potassium carbonate at room temperature for 72 hours, then dilute sodium hydroxide solution was added, the mixture was shaken with methylene chloride, the organic phase was washed with water and dried, and the solvent was removed by distillation. The residue of 7.0 g was chromatographed in methylene chloride on a column containing silica gel, and 4.6 g of pure 4-methyl-6-[4-(1-naphthylmethoxy)phenoxymethyl]-2-pyrone of melting point 132° C. were obtained. This product was heated with 15 g of 2-aminopyridine at 75° C. and, during stirring for 32 hours, 7 g of hydroxylamine hydrochloride were added in 4 portions. After the reaction had lasted a total of 42 hours, the residue was taken up in methylene chloride, and the solution was washed with dilute hydrochloric acid and water and dried, the solvent was removed by distillation, and the residue was recrystallized from acetonitrile. 1.9 g of the pure compound 10, of melting point 179° C., were isolated.

21–30

In the same manner as in Example 20, the compounds 5, 8, 15, 16, 17, 27, 46 and 52 were obtained by alkylation of the intermediate 6-(4-hydroxyphenoxymethyl)-4-methyl-2-pyrone with the chlorides 2,4-dichlorobenzyl chloride, cinnamyl chloride, 4-chlorobenzyl chloride, 4-trifluoromethoxybenzyl chloride, 4-tert.-butylbenzyl chloride, 3,4,5-trimethoxybenzyl chloride, 1-chloro-3-(4-chlorophenoxy)propane and 1-chloro-4-(4-chlorophenoxy)-2-butene and conversion of the resulting pyrones into the hydroxypyridones. Use of catechol in place of hydroquinone and alkylation with 1-naphthylmethyl chloride resulted in compound 19, and resorcinol and 4-chlorobenzyl chloride resulted in compound 21.

31:
6-[2,6-Dichloro-4-(2-naphthylthiomethyl)phenoxymethyl]-1-hydroxy-4-methyl-2-pyridone (compound 13)

4.8 g of sodium and 42 g of 3,5-dichloro-4-hydroxybenzaldehyde were dissolved in 250 ml of methanol, the solvent was removed by distillation under reduced pressure, the residue was taken up in 200 ml of dimethylformamide, 32 g of 6-chloromethyl-4-methyl-2-pyrone were added, and the mixture was left to react at room temperature for 3 days. The dimethylformamide was then substantially removed by distillation under reduced pressure, methanol was added, and a total of 44 g of 6-(2,6-dichloro-4-formylphenoxymethyl)-4-methyl-2-pyrone of melting point 180° C. was isolated in several fractions by cooling and concentration of the mother liquor. 34.5 g of this compound were reduced in a mixture of 250 ml of tetrahydrofuran and 100 ml of methanol using 1.5 g of sodium borohydride at room temperature, the mixture was subsequently heated to 50° C., then 10 ml of concentrated sulfuric acid were added, most of the solvent was removed by distillation, the residue was shaken with water, and the solid was filtered off with suction, washed with water and dried. This product (33.1 g, melting point 154° C.) was suspended in 200 ml of methylene chloride, and 0.1 ml of dimethylformamide and then, at room temperature, 11 ml, in portions, of thionyl chloride were added. After 24 hours, the solvent was removed by distillation, the residue was boiled with 200 ml of methanol, the mixture was cooled to 0° C., and the product was filtered off with suction, washed and dried. 30.1 g of pure 6-(2,6-dichloro-4-chloromethylphenoxymethyl)-4-methyl-2-pyrone of melting point 136° C. were obtained.

7.5 g of the resulting compound were stirred with 4 g of 2-thionaphthol, 30 ml of dimethylformamide and 7 g of potassium carbonate at room temperature for 24 hours, then water was added, and the mixture was shaken with methylene chloride, and the solution was washed with water, dried and chromatographed on a column containing silica gel. 8.5 g of 6-[2,6-dichloro-4-(2-naphthylthiomethyl)phenoxymethyl]-4-methyl-2-pyrone of melting point 125° C. were obtained. This product was heated with 25 g of 2-aminopyridine at 75° C. and, within 37 hours, a total of 8 g of hydroxylamine hydrochloride was added in 4 portions. After the reaction had lasted 48 hours, the residue was taken up in methylene chloride, the organic phase was washed with dilute hydrochloric acid and water and was dried, and the solvent was removed by distillation. The residue was recrystallized once from acetonitrile and once from ethyl acetate, and in this way 2.1 g of the pure compound 13 of melting point 138° C. were obtained.

32 and 33

In analogy to the procedure of Example 31, the compound 14 was obtained by reaction of the intermediate 6-(2,6-dichloro-4-chloromethylphenoxymethyl)-4-methyl-2-pyrone with 4-phenylphenol and conversion of the resulting pyrone into the hydroxypyridone. Use of 4-hydroxybenzaldehyde in place of 3,5-dichloro-4-hydroxybenzaldehyde, and analogous reduction, reaction with thionyl chloride, condensation with 4-(4-chlorophenoxy)phenol and reaction with hydroxylamine provided compound 12.

34:
6-[4-(4-Chlorophenoxy)phenoxymethyl]-1-hydroxy-2-pyridone (compound 22)

30 g of 2-bromo-6-picoline were heated to reflux with 31.6 g of N-bromosuccinimide, 0.015 g of dibenzoyl peroxide and 150 ml of carbon tetrachloride under UV irradiation for 30 hours, the mixture was filtered, the filtrate was washed once with aqueous sodium carbonate solution and three times with water, and was dried, and the solvent was removed by distillation under reduced pressure. The residue (40.1 g) was shaken with 150 ml of hexane, and filtration with suction produced 27.3 g of a mixture which was composed mainly of the desired monobromomethyl compound in addition to a little dibromomethyl compound. This mixture was stirred together with 21.4 g of 4-(4-chlorophenoxy)-phenol, 20.7 g of potassium carbonate and 50 ml of dimethylformamide at room temperature for 48 hours, then 200 ml of methylene chloride were added, and the organic solution was washed three times with water and concentrated, and 16.3 g of 2-bromo-6-[4-(4-chlorophenoxy)phenoxymethyl]pyridine were isolated by chromatography on silica gel and recrystallization from diisopropyl ether.

15.8 g of the resulting compound were heated with a solution of 8.5 g of peracetic acid in 50 ml of glacial acetic acid at 50° C. for 30 hours, then the solvent was partially removed by distillation under reduced pressure at 40° C., the residue was shaken three times with 200 ml of water each time, and once with aqueous sodium bicarbonate solution, decanting off each time, and was finally treated with 100 ml of diisopropyl ether, and the product was filtered off with suction and dried. 10.2 g of almost pure N-oxide of melting point 100° C. were obtained in this way. 5 g of this N-oxide were heated with a solution of 1.2 g of sodium hydroxide in a mixture of 9 ml of water and 20 ml of ethylene glycol monomethyl ether at 70° C. During this, reaction with the alcohol resulted in rapid formation of the methoxyethyl ether of the N-oxide, which melted at 125° C., and the ether was then slowly hydrolyzed. After 60 hours, the solvent was removed by distillation under reduced pressure, the residue was shaken with 200 ml of methylene chloride and 50 ml of dilute sulfuric acid, and the organic phase was separated off, dried and evaporated. The residue was recrystallized from acetonitrile, and 2.5 g of the pure compound 22 of melting point 180° C. were obtained.

35:
1-Hydroxy-4-methyl-6-[3-(1-naphthylmethoxy)-phenylthiomethyl]-2-pyridone 26 g of monothioresorcinol and 31.8 g of 6-chloromethyl-4-methyl-2-pyrone were dissolved in 100 ml of dimethylformamide and, while stirring and cooling in ice, 38 g of powdered potassium carbonate were added within 30 minutes, then the mixture was stirred at 0° C. for 4 hours and at room temperature for 16 hours, then 300 ml of methylene chloride were added, and the organic phase was extracted by shaking three times with water, separated off and dried, and the solvent was removed by distillation. The residue was recrystallized from methanol, and 44 g of 6-(3-hydroxyphenylthiomethyl)-4-methyl-2-pyrone, compound (C) of melting point 129° C., were obtained. 8.9 g of 1-chloromethylnaphthalene were added to a solution of 8 g of sodium iodide in 200 ml of acetone, the mixture was stirred at room temperature for 16 hours, and then 12.4 g of compound C were dissolved in the mixture, which was cooled to 0° C. and 6.9 g of powdered potassium carbonate were added in portions within 5 hours. After a total reaction time of 79 hours at 0° C., the solvent was removed by distillation under waterpump vacuum, the residue was taken up in methylene chloride, and the solution was washed with water, separated off, dried and concentrated, and the product as chromatographed on a column containing silica gel and using methylene chloride as mobile phase, and the main fractions were recrystallized from methanol. 9 g of pure 4-methyl-6-[3-(1-naphthylmethoxy)-phenylthiomethyl]-2-pyrone of melting point 139° C. were obtained.

8.5 g of this compound were heated with 50 g of 2-aminopyridine at 75° C. and, within 40 hours, 8.9 g of hydroxylamine hydrochloride were added in portions. After a reaction time of 60 hours, the mixture was cooled to room temperature, methylene chloride was added, and the organic phase was washed once with dilute hydrochloric acid and three times with water and was dried, and the solvent was removed by distillation. The residue was recrystallized from ethyl acetate, and 4 g of hydroxypyridone of melting point 163° C. were obtained.

36

When the pyrone C (cf. Example 35) was reacted with 4-chlorobenzyl chloride and the remainder of the process was carried out as in Example 35, compound 42 was obtained.

37:
1-Hydroxy-4-methyl-6-[4-(4-chlorophenoxy)phenoxymethyl]-2-pyridone 171.4 g (0.5 mole) of 4-methyl-6-[4-(4-chlorophenoxy)phenoxymethyl]-2-pyrone in 50 ml of toluene were heated to 80° C. Then 59.9 g (0.36 mole) of hydroxylammonium sulfate and 38.3 g (0.36 mole) of sodium carbonate were added. 10 minutes later a further 59.9 g (0.36 mole) of hydroxylammonium sulfate and 38.3 g (0.36 mole) of sodium carbonate were added. After about 4 hours the heating was removed and, at about 40° C., 500 ml of methylene chloride were added. The dissolved reaction product was then filtered off from the insoluble salts. The filtrate was then dried over sodium sulfate, and the methylene chloride was evaporated off. When the residue was stirred with 500 ml of ethyl acetate, the reaction product crystallized out. For final purification, the 1-hydroxy-4-methyl-6-[4-(4-chlorophenoxy)phenoxymethyl]-2-pyridone was recrystallized from dimethylformamide. Yield 80.5 g (45%); melting point 168°–170° C.

38:
1-Hydroxy-4-methyl-6-[3-(2-phenoxyethoxy)phenoxymethyl]-2-pyridone (compound 45)

A mixture of 80 g of 6-chloromethyl-4-methyl-2-pyrone, 220 g of resorcinol, 400 ml of dimethylformamide and 105 g of finely ground potassium carbonate was stirred at room temperature for 72 hours, then methylene chloride was added, and the organic phase was extracted by shaking several times with water and dried, and the solvent was removed by distillation under reduced pressure. The viscous residue (223 g) was triturated with water and then recrystallized from methanol, and 53 g of 6-(3-hydroxyphenoxymethyl)-4-methyl-2-pyrone (compound D) of melting point 145° C. were isolated. 10 g of compound D were stirred with 11.2 g of 1-iodo-2-phenoxyethane (prepared by reaction of 2-phenoxyethanol with $SOCl_2$ followed by replacement of chlorine by iodine with sodium iodide in acetone), 6.9 g of potassium carbonate and 50 ml of dimethylformamide at 50° C. for 35 hours, methylene chloride was added, and the solution was washed several times with water, dried and chromatographed on silica gel. The main product isolated was 10.4 g of 4-methyl-6-[3-(2-phenoxyethoxy)phenoxymethyl]-2-pyrone of melting point 95° C. 10 g of this pyrone were heated with 50 g of 2-aminopyridine at 75° C. for 63 hours while adding 8.5 g of hydroxylamine hydrochloride in portions, the residue was then taken up in methylene chloride, and the solution was extracted by shaking with dilute hydrochloric acid (pH of the aqueous phase 3 to 4) and dried, and the solvent was removed by distillation, and the residue was crystallized from acetonitrile. 4.3 g of the pure hydroxypyridone of melting point 148° C. were obtained.

39 and 40

In the same manner as in Example 38, the compound 48 was obtained starting from the intermediate D and 1-(4-chlorophenylthio)-4-iodobutane, and the compound 49 was obtained from D and 2-(4-chlorophenylthio)ethyl 2'-iodoethyl ether.

41:
6-[3-(4-Chlorophenylthiopropylthio)phenoxymethyl]-1-hydroxy-4-methyl-2-pyridone (compound 47)

A mixture of 12.6 g of monothioresorcinol, 31.3 g of 1-(4-chlorophenylthio)-3-iodopropane (prepared from 4-chlorothiophenol and 1-bromo-3-chloropropane followed by replacement of chlorine by iodine with sodium iodide in acetone), 16.6 g of potassium carbonate and 60 ml of acetone was stirred at room temperature for 24 hours, then the solvent was removed by distillation under reduced pressure, methylene chloride was added, the solution was washed several times with water and dried, and then 14.5 g of 3-(4-chlorophenylthiopropylthio)phenol were isolated by chromatography on silica gel using methylene chloride as mobile phase. This product was stirred together with 9.5 g of 6-chloromethyl-4-methyl-2-pyrone, 10.4 g of potassium carbonate and 60 ml of acetone at 50° C. for 31 hours, then the solvent was removed by distillation under reduced pressure, the residue was taken up in methylene chloride, and the solution was washed several times with water, dried and chromatographed on silica gel. 11.2 g of the main fraction were heated with 50 g of 2-aminopyridine at 75° C. for 65 hours, and a total of 12 g of hydroxylamine hydrochloride was added in several portions. The residue was then taken up in methylene chloride, and the organic phase was extracted by shaking with dilute hydrochloric acid and several times with water and was dried, and the solvent was removed by distillation. The residue amounted to 9.9 g. Treatment with methanol resulted in 2.7 g of pure hydroxypyridone of melting point 102° C.

42 and 43

With the same reaction sequence and under the same conditions, the compound 51 was obtained starting from monothioresorcinol and 1-(4-chlorophenylthio)-2,2-dimethyl-3-iodopropane, and the compound 53 was obtained from monothioresorcinol and (4-chlorophenylthio)ethoxyethoxyethyl iodide.

Investigation of the activity

In the in vitro investigation of antimycotic substances, it is necessary to distinguish between an effect on proliferating microorganisms (fungistasis) and resting microorganisms (fungicidal activity).

The fungicidal activity, tested on the non-growing fungus, is categorized as the more stringent model. This entails a dilution series of the products which are to be tested being made up in microtiter plates (31.25 to 0.25 µg/ml; 8 steps). Each U-shaped well on the plate is inoculated with $10^4$ colony-forming units (CFU) of the skin fungus Trichophyton mentagrophytes (medium: physiol. NaCl solution). After incubation at 30° C. for 18 h, the microorganisms are washed with 50% polyethylene glycol 400 and NaCl solution (two centrifugations) and, to determine the microorganism count, streaked on malt-agar plates using an automatic device. After incubation at 30° C. for 3 days, the colonies are counted, and the CFU/ml is calculated. By comparison with the untreated control, the per cent reduction in the microorganism count is determined (control=0%). The strength of action is measured by standard products, for example clotrimazole; clotrimazole is the generic name of the compound of the formula

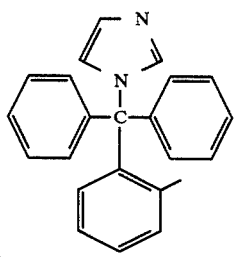

As is evident from Table 1, the compounds according to the invention showed an extremely low number of CFU in relation to the standard product clotrimazole, i.e. the fungicidal or lethal effect of the compounds according to the invention is distinctly more pronounced than that of the standard agent.

TABLE 1

| Product No. | Number of CFU/ml $\bar{x}$ (n = 4) | Reduction in CFU compared with control, in % |
| --- | --- | --- |
| 1 | 0 | 100 |
| 9 | 0 | 100 |
| 15 | 1 | 99.32 |
| 17 | 1.5 | 98.98 |
| clotrimazole | 63.6 | 57 |
| untreated control | 147.9 | 0 |

$\underline{n}$ = number of measurements
$\bar{x}$ = mean

As an example of the high topical in vivo activity of the compounds according to the invention, results of treatment of laboratory animals experimentally infected with Trichophyton mentagrophytes are detailed. This entailed two or four guineapigs (Pirbright white strain) weighing 450–500 g each being infected with $1.5 \times 10^4$ conidia/animal in the epidermis, distributed over 6 infection points in each case. The animals were treated 4 and 3 days before the infection by application of a 0.3% strength solution of the product on 3 infection sites on the right side of the back on each occasion. The left side of the back, with 3 infection sites in each case, was treated in the same way with vehicle containing no product (vehicle control).

In addition to the animals treated with the substances according to the invention, two animals were treated with the reference substance clotrimazole, and two infected animals remained untreated (infection control).

As is evident from Table 2, the compounds according to the invention showed a distinctly greater difference in the diameter of the mycoses (mm) than did the standard product clotrimazole, i.e. the antimycotic effect of the compounds according to the invention was unambiguously superior to that of clotrimazole.

TABLE 2

| Concentration | Product No. | Number of animals | Vehicle control n | $\bar{x}_1$ | (s) | Product + vehicle n | $\bar{x}_2$ | (s) | Difference $\bar{x}_1 - \bar{x}_2$ (%) |
| --- | --- | --- | --- | --- | --- | --- | --- | --- | --- |
| Dermal 2 × 0.3% | 1 | 4 | 12 | 14.8 | (2.7) | 12 | 9.2 | (3.4) | 5.6 (160.0) |
| | 3 | 4 | 12 | 13.7 | (2.2) | 12 | 8.3 | (1.2) | 5.4 (154.2) |
| | 9 | 2 | 6 | 14.0 | (3.4) | 6 | 9.1 | (1.8) | 4.9 (140.0) |
| | 26 | 2 | 6 | 15.0 | (1.5) | 6 | 7.8 | (0.4) | 7.2 (205.7) |
| | clotrimazole | 4 | 12 | 13.9 | (2.0) | 12 | 10.4 | (1.8) | 3.5 (100.0) |
| Infection control | — | 2 | 12 | 13.7 | (1.1) | | | | |

$\underline{n}$ = number of measurements
$\bar{x}$ = mean
(s) = standard deviation

We claim:

1. A 1-hydroxy-2-pyridone of the formula I

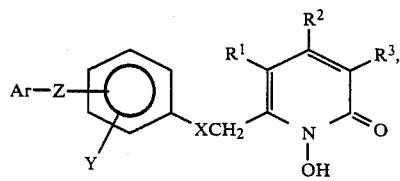

in which
- $R^1$, $R^2$ and $R^3$, which are identical or different, denote hydrogen or lower alkyl having 1–4 carbon atoms,
- X denotes S or O,
- Y denotes hydrogen or up to 2 halogen atoms selected from chlorine and bromine,
- Z denotes a single bond or the bivalent radicals O, S, $-C(R)_2-$ wherein R is H or $C_1-C_4$-alkyl, or denotes other bivalent radicals with 2–10 carbon atoms linked to form a chain or said other bivalent radicals containing 2–10 carbon atoms and oxygen or sulfur atoms linked to form a chain, with the proviso that when the radicals contain 2 or more oxygen or sulfur atoms, said oxygen or sulfur atoms are separated by at least 2 carbon atoms, or denotes said other bivalent radicals having 2 adjacent carbon atoms linked together by a double bond, with the free valencies of the carbon atoms being saturated by H or $C_1-C_4$-alkyl groups,
- Ar denotes a fused or an isolated aromatic ring system selected from the group consisting of phenyl, naphthyl, tetrahydronaphthyl, indenyl, biphenyl, diphenylalkane, diphenylether and diphenylthioether, or said fused or isolated aromatic ring system substituted by up to three radicals selected from the group consisting of fluorine, chlorine, bromine, methoxy, $C_1-C_4$-alkyl, trifluoromethyl and trifluoromethoxy.

2. A compound as claimed in claim 1, wherein Ar represents the phenyl ring or said phenyl ring substituted by up to three radicals from the group consisting of fluorine, chlorine, bromine, methoxy, $C_1-C_4$-alkyl, trifluoromethyl and trifluoromethoxy.

3. A compound as claimed in claim 1, wherein Ar represents an isolated bicyclic system derived from biphenyl, diphenylalkane or diphenyl ether or said isolated bicyclic system substituted by up to three radicals from the group consisting of fluorine, chlorine, bromine, methoxy, $C_1-C_4$-alkyl, trifluoromethyl and trifluoromethoxy.

4. A compound as claimed in claim 1, wherein Z is a single bond.

5. A compound as claimed in claim 1, wherein Z represents or contains oxygen.

6. 6-[4-(4-Chlorophenoxy)phenoxymethyl]-1-hydroxy-4-methyl-2-pyridone (=compound of the formula I as defined in claim 1 with $R^1=R^3=Y=H$, $R^2=CH_3$, X=O, Z=O in the 4-position to the $XCH_2$ group, and Ar=

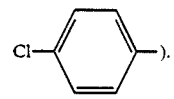

7. 6-[4-(Biphenylyloxymethyl)-1-hydroxy-4-methyl-2-pyridone (=compound of the formula I as defined in claim 1 with $R^1=R^3=Y=H$, $R^2=CH_3$, X=O, Z=single bond, and Ar=$C_6H_5$ in the 4-position to the $XCH_2$ group).

8. 1-Hydroxy-4-methyl-6-[4-(4-trifluoromethylphenoxy)phenoxymethyl]-2-pyridone (=compound of the formula I as defined in claim 1 wherein $R^1=R^3=Y=H$, $R^2=CH_3$, X=O, Z=O in the 4-position to the $XCH_2$ group, and Ar=

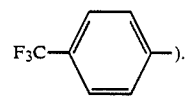

9. A method of controlling infections by fungi and yeasts in a mammal which comprises administering to said mammal an effective amount for said controlling of a compound of the formula I as claimed in claim 1, a physiologically tolerated salt of said compound with an inorganic or organic base, or a mixture thereof.

10. A medicament for controlling infections in humans and animals containing as active ingredient an effective amount for said controlling of at least one compound of the formula I as claimed in claim 1, a physiologically tolerated salt of said compound with an inorganic or organic base, or a mixture of said compound and said salt, in combination with a physiologically acceptable vehicle.

11. A medicament as claimed in claim 10 for use as an antimycotic.

12. A medicament as claimed in claim 10 for treating pathogenic skin fungi and mucous membrane fungi.

13. A compound as claimed in claim 1, wherein $R^1$ and $R^3$ denote hydrogen.

14. A compound as claimed in claim 1, wherein $R^2$ denotes methyl.

15. A compound as claimed in claim 1, wherein X denotes O.

* * * * *